United States Patent [19]

Hart et al.

[11] Patent Number: 5,476,988
[45] Date of Patent: Dec. 19, 1995

[54] SETTLING AIDS FOR SOLIDS IN HYDROCARBONS

[75] Inventors: Paul R. Hart, The Woodlands; Wiley L. Parker, Conroe; Alan E. Goliaszewski, The Woodlands; April Jean; Scott E. Lehrer, both of Houston, all of Tex.

[73] Assignee: Betz Laboratories, Inc., Trevose, Pa.

[21] Appl. No.: 248,927

[22] Filed: May 25, 1994

[51] Int. Cl.$^6$ .............................. C07C 7/00; C10G 29/00
[52] U.S. Cl. .............................. 585/860; 585/4; 585/833; 208/180; 208/289
[58] Field of Search .............................. 585/4, 818, 833, 585/860; 208/180, 251 R, 262.1, 289

[56] References Cited

U.S. PATENT DOCUMENTS

| | | | |
|---|---|---|---|
| 3,363,021 | 1/1968 | Tucci | 260/677 |
| 3,539,653 | 11/1970 | Frevel et al. | 585/860 |
| 5,196,630 | 3/1993 | Agrawal et al. | 585/860 |

FOREIGN PATENT DOCUMENTS

| | | |
|---|---|---|
| 0083422 | 7/1981 | Japan. |

*Primary Examiner*—P. Achutamurthy
*Attorney, Agent, or Firm*—Alexander D. Ricci; Philip H. Von Neida

[57] ABSTRACT

A method for accelerating the settling of finely divided solids in hydrocarbon fluids comprising adding to the hydrocarbon a sufficient settling amount of quaternary fatty ammonium compound. Preferably, the hydrocarbon is a fluid catalytic cracker slurry containing spent catalyst fines.

10 Claims, No Drawings

SETTLING AIDS FOR SOLIDS IN HYDROCARBONS

FIELD OF THE INVENTION

The present invention relates to methods for accelerating settling of solids in hydrocarbon fluids. The methods of the present invention are particularly efficacious at accelerating the settling of FCC catalyst fines in an oil slurry.

BACKGROUND OF THE INVENTION

Unrefined hydrocarbons such as crude oil, resids and bottom streams often contain finely divided solid matter which often must be removed prior to further use or processing. These solids can include solids of a soil-like nature, finely divided silicas, clays, silt and coke, and metal oxide and sulfide corrosion solids. These solids may include traces of metal particles such as lead, nickel, chromium and the like, and salts thereof.

For instance, fluid catalytic cracker (FCC) units use a fluidized bed of zeolite type aluminosilicate clay particles to crack heavy petroleum fractions into lighter fractions at elevated temperatures. The catalyst is eventually deactivated by poisoning or coking. These spent fines must be removed from the FCC on a continual basis so that fresh catalyst can be added.

Some of this slurry oil containing the spent fines is then typically
settled in tankage, though hydrocyclones are sometimes used to accelerate the separation process. Both native and synthetic components of the slurry oil have a dispersant effect which retards the settling of the fines.

The present inventors have discovered that certain chemical agents, when added to the slurry oil, have an anti-dispersant or coagulent effect which accelerates the settling process. This produces a cleaner decant oil (typically <0.05 wt % ash) in a shorter period of time and can then be sold as carbon black feedstock or residual fuel oil.

DETAILED DESCRIPTION OF THE INVENTION

The present invention relates to methods for accelerating the settling of finely divided solids in hydrocarbon fluids comprising adding a quaternary fatty ammonium compound to the hydrocarbons. More particularly, the present invention provides methods for accelerating the settling of spent fluid catalytic cracker (FCC) catalyst fines present in an oil slurry comprising adding to the slurry a quaternary fatty ammonium compound.

The quaternary fatty ammonium compounds are generally quaternary ammonium compounds having the formula

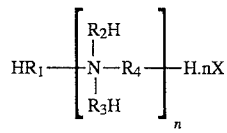

where $R_1$, $R_2$, $R_3$ and $R_4$ can be $-R_5-$, $-(R_5O)-_m$, or

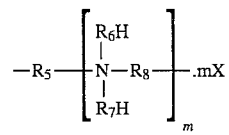

where $R_5$, $R_6$, $R_7$ and $R_8$ can be $C_1$ to $C_{30}$ alkylene, alkenylene, or alkylarylidene, and m is 1–25, X is a halide, sulfate, nitrate, phosphate or carboxylate anion, and n is 1–50.

The particular quaternary fatty ammonium compounds of the present invention are effective at accelerating settling of finely divided solids, particularly FCC catalyst fines. These compounds include but are not limited to methyl quaternary amine ethoxylates such as tallow triethoxyl quaternary amine acetate and a hydrogenated $C_{18}$ methyl chloride quaternary amine with 15 moles ethylene oxide, both available from Akzo as Ethoquad T/13 and 18/25, respectively; and tallow and $C_{18}$ amine alkyl quaternary compounds such as tallow aminopropylamine pentamethyl dichloride, tallow diaminopropylamine heptamethyl trichloride and $C_{18}$ aminopropylbisaminopropylamine nonamethyl tetrastearate. These compounds are effective settling aids either singly or in a combination of two or more quaternary fatty ammonium compounds.

An example of a combination of effective quaternary fatty ammonium compounds is a 1:2 blend based on actives of a tallow triethoxyl quaternary amine acetate and a hydrogenated $C_{18}$ methyl chloride quaternary amine with 15 moles ethylene oxide.

The quaternary fatty ammonium compounds prove effective in a variety of hydrocarbon fluids. These hydrocarbon fluids are generally unrefined hydrocarbons that are prone to containing finely divided solids. These hydrocarbon fluids include but are not limited to FCC slurries, crude oils, resids, bottom streams, vacuum bottoms, heavy ends, and the like. The quaternary fatty ammonium compounds are expected to provide efficacy at hydrocarbon temperatures ranging from ambient to 600° F.

Actual dosage ranges for the quaternary fatty ammonium compounds depend upon the characteristics of the hydrocarbon to be treated. These characteristics can vary and include the type of hydrocarbon, the type and amount of finely divided solid present, and the presence of other impurities and surfactants in the hydrocarbon. Preferably, about 1 part to about 500 parts of the quaternary fatty ammonium compound per million parts of the hydrocarbon are added. Different hydrocarbons will surely have different optimum dosage ranges.

The quaternary fatty ammonium compounds can be fed to the hydrocarbon to be treated neat or in a suitable solvent that is compatible with the treatment and the hydrocarbon. Examples of such solvents include but are not limited to linear or branched chain aliphatic and aromatic solvents such as naphtha, toluene, xylene and the like.

The compounds of the present invention can be used in conjunction with other hydrocarbon treatment chemicals particularly flocculants which can be inorganic or organic and include any material that enhances aggregation of finely dissolved solids to form a floc and enhance settling of solids and phase separation or transfer, and demulsifiers, which can be any material that accelerates the settling of water with which the solids can be associated.

The following examples are intended to show the efficacy of the present invention as an accelerator for settling finely divided solids in hydrocarbons and should not be construed as limited the scope of the invention.

EXAMPLES

Catalyst Settling Aid Test.

This test measures the fraction of FCC catalyst fines which settle to the bottom of a slurry sample compared to the amount which remains dispersed on top. This test simulates slurry settling in tankage between ambient temperature and 200° F.

Experimental

Collect 100 mL of FCCU slurry in 6 oz. bottles. Place bottles in a water bath and heat to process temperature. Remove each bottle from the bath and add the appropriate treatment to the desired bottles. Place the bottles in an insulated shaker and shake on high speed setting for 10 minutes. Return the bottles to the bath and allow to stand undisturbed for the predetermined settling period. This predetermined settling time for a blank is determined by analyzing several untreated bottles according to this test procedure at various time intervals centered on the tank's residence time (e.g., 5 hours, 1 day, 3 days, 7 days).

Test methods vary in the point at which the sample is split between the top and bottom portions for analysis at the end of the settling period. The size of the top portion is used to designate the method use. For example, "50% method", "95% method", "20% method", and "10% method". For most samples, the 50% method described below is used. For extremely fast settling samples, use a short settling time and the 95% method described below. For very slow settling samples, use a long settling time and the 20% or 10% variation of the 50% method.

50% method (or 20% or 10%)

Pipet off the top 50 mLs (top sample) with a syringe being careful not to disturb the sample or insert the needle below the 50 (or 80 or 90) mL line, and transfer to a clean bottle. The original bottle contains the bottom sample.

95% method

Pour off ~95 mLs into a clean bottle (top sample). The remaining ~5 mLs in the original bottle is the bottom sample.

Place filter pads in small petri dishes, dry uncovered at 220° F. for one hour, remove from oven and allow to cool in a desiccator. Weigh and record filter weight.

Place filter in a paraloid filtration funnel and wet with xylene or toluene to ensure a good seal for vacuum filtration. Shake the oil sample vigorously and carefully pour it up to 50 mL at a time into a graduated centrifuge tube, then double the volume, up to 100 mL, with xylene or toluene.

Heat the centrifuge tube to 180° F. in a water bath. Centrifuge for 15 minutes. Turn on the vacuum pump and pour a small amount of hot oil from the centrifuge tube into the filter funnel and allow it to filter. Rinse with xylene or toluene. Continue adding small amounts and rinsing until all the sample has been filtered. Then rinse centrifuge tube and funnel with more xylene or toluene until it is clean. Remove filter bowl and wash, under vacuum, the filter pad with xylene or toluene followed by petroleum ether or heptane. Dry filter pad in an oven at 220° F. for one hour. Allow to cool in a desiccator and reweigh.

Place the filters in glass petri dishes and ash in a muffle furnace at ~900° F. Weigh again to determine catalyst weights, being careful not to disturb loose ash on filters.

The % settled is calculated by the following methods:

| 50% Method | 20% Method | 95% Method |
|---|---|---|
| % settled = | % settled = | % settled = |
| $\dfrac{\text{bottom} - \text{top(g)}}{\text{bottom} + \text{top(g)}}$ | $\dfrac{\text{bottom} - 4 \times \text{top(g)}}{\text{bottom} + \text{top(g)}}$ | $\dfrac{\text{bottom} - (5/95) \times \text{top(g)}}{\text{bottom} + \text{top(g)}}$ |

A settling period which yields about 40 to 50% settled should be chosen. Repeat the optimal procedure determined from the blanks after adding chemical treatments at the process dosage.

Testing was performed utilizing the compounds of the instant invention and commercially available compounds such as DB-7935 from BASF which is a nonylphenol-formaldehyde resin ethoxylate.

TABLE I

Southern Refinery
FCCU catalyst slurry settling study
Settled 160° F. for 1 day
50 and 95% methods

| Treatment (ppm) | 130–140 total volume weight ash in mg | | | % Settled from top 50% to Bottom 50% | % Settled from top 96% to Bottom 4% |
|---|---|---|---|---|---|
| | 70 mL (top) | 55–65 (mid) | 5 mL (bot) | | |
| Blank (0) | 47.5 | 37.2 | 87.0 | 45 | 49 |
| | 45.5 | 36.8 | 85.0 | 46 | 49 |
| Comp 1 | 47.9 | 38.8 | 151.8* | 60* | 62 |
| (75) | 45.8 | 25.1 | 69.6 | 35 | 47 |
| A (37.5) | 41.7 | 32.9 | 90.8 | 50 | 53 |
| | 41.0 | 31.1 | 87.3 | 49 | 53 |

Comp 1 is a commercially available nonylphenol-formaldehyde ethoxylate
Treatment A is a 1:2 blend (actives) of a tallow triethoxyl quaternary amine acetate and a hydrogenated $C_{18}$ methyl chloride quaternary amine with 15 moles ethylene oxide.
*probable chunk in bottle which fell to bottom.

As seen in Table I, the quaternary fatty compounds of this invention proved more effective and more efficient at settling the slurry than conventional compounds.

TABLE II

Midwest refinery
Slurry settling
24 hours settling time at 200° F.
95% method - filterable solids

| Treatment (ppm) | Total wt (g) | Top 95% wt (g) | Top 95% wt (% solids) | Bot 5% wt (g) | Bot 5% wt (% solids) | % Settled |
|---|---|---|---|---|---|---|
| Blank | 0.2410 | 0.1868 | 77.50 | 0.0542 | 22.5 | 18 |
| Comp 1 (30) | 0.2550 | 0.2007 | 78.70 | 0.0543 | 21.3 | 17 |
| Comp 2 (30) | 0.2277 | 0.1758 | 77.20 | 0.0519 | 22.8 | 19 |
| A (15) | 0.2405 | 0.1805 | 75.10 | 0.0600 | 24.9 | 21 |

Comps 1 and 2 are commercially available nonylphenol-formaldehyde ethoxylates.
Treatment A is a 1:2 blend (actives) of a tallow triethoxyl quaternary amine acetate and a hydrogenated $C_{18}$ methyl chloride quaternary amine with 15 moles ethylene oxide.

TABLE III

Midwest refinery
Slurry settling
24 hours settling time at 200° F.
95% method - ash

| Treatment (ppm) | Total wt (g) | Top 95% wt (g) | Top 95% wt (% ash) | Bot 5% wt (g) | Bot 5% wt (% ash) | % Settled |
|---|---|---|---|---|---|---|
| Blank | 0.2269 | 0.1780 | 78.40 | 0.0489 | 21.60 | 17 |
| Comp 1 (30) | 0.2397 | 0.1904 | 79.40 | 0.0493 | 20.60 | 16 |
| Comp 2 (30) | 0.2139 | 0.1671 | 78.10 | 0.0468 | 21.90 | 18 |
| A (15) | 0.2268 | 0.1720 | 75.80 | 0.0548 | 24.20 | 20 |

Comps 1 and 2 are commercially available nonylphenol-formaldehyde ethoxylates.
Treatment A is a 1:2 blend (actives) of a tallow triethoxyl quaternary amine acetate and a hydrogenated $C_{18}$ methyl chloride quaternary amine with 15 moles ethylene oxide.

As seen in Tables II and III, the quaternary fatty ammonium compounds of the present invention provide equal to or better settling acceleration of FCC slurry fines than conventional treatment aids at a lower dosage.

TABLE IV

Midwest refinery
Slurry settling
24 hours settling time at 200° F.
95% method - filterable solids

| Treatment (ppm) | Total wt (g) | Top 95% wt (g) | Top 95% wt (% solids) | Bot 5% wt (g) | Bot 5% wt (% solids) | % Settled |
|---|---|---|---|---|---|---|
| Blank | 0.2021 | 0.1654 | 81.80 | 0.0367 | 18.20 | 14 |
| Comp 1 (75) | 0.2038 | 0.1520 | 74.60 | 0.0518 | 25.40 | 21 |
| Comp 2 (75) | 0.2093 | 0.1165 | 55.70 | 0.0928 | 44.30 | 41 |
| A (37.5) | 0.2068 | 0.1301 | 62.90 | 0.0767 | 37.10 | 34 |

Comps 1 and 2 are commercially available nonylphenol-formaldehyde ethoxylates.
Treatment A is a 1:2 blend (actives) of a tallow triethoxyl quaternary amine acetate and a hydrogenated $C_{18}$ methyl chloride quaternary amine with 15 moles ethylene oxide.

TABLE V

Midwest refinery
Slurry settling
24 hours settling time at 200° F.
95% method - filterable solids

| Treatment (ppm) | Total wt (g) | Top 95% wt (g) | Top 95% wt (% ash) | Bot 5% wt (g) | Bot 5% wt (% ash) | % Settled |
|---|---|---|---|---|---|---|
| Blank | 0.1896 | 0.1569 | 82.80 | 0.0327 | 17.20 | 13 |
| Comp 1 (75) | 0.1924 | 0.1447 | 75.20 | 0.0477 | 24.80 | 21 |
| Comp 2 (75) | 0.1966 | 0.1111 | 56.50 | 0.0855 | 43.50 | 41 |
| A (37.5) | 0.1955 | 0.1245 | 63.70 | 0.0710 | 36.60 | 33 |

Comps 1 and 2 are commercially available nonylphenol-formaldehyde ethoxylates.?
Treatment A is a 1:2 blend (actives) of a tallow triethoxyl quaternary amine acetate and a hydrogenated $C_{18}$ methyl chloride quaternary amine with 15 moles ethylene oxide.

TABLE VI

Southern refinery
Slurry settling
24 hours settling time at 135° F.
Top 10% remoded and analyzed for solids (bottom not analyzed)

| Treatment (ppm) | Top 10% (mg solids) | Next 40% (mg solids)[1] | Top 50% (mg solids)[2] | % Reduction From Blank |
|---|---|---|---|---|
| Blank | 0.0056 | | | — |
| A (15) | 0.0037 | | | 33.93 |
| A (15) | 0.0049 | | | 12.50 |
| A (37.5) | 0.0042 | | | 25.00 |
| A (37.5) | 0.0042 | | | 25.00 |
| A (75) | 0.0041 | | | 26.79 |
| A (75) | 0.0035 | | | 37.50 |
| Comp 1 (30) | 0.0053 | | | 5.36 |
| Comp 1 (30) | 0.0061 | | | −8.93 |
| Comp 1 (75) | 0.0059 | | | −5.36 |
| Comp 1 (75) | 0.0057 | | | −1.79 |
| Comp 1 (150) | 0.0053 | | | 5.36 |
| Comp 1 (150) | 0.0050 | | | 10.71 |
| Comp 2 (35) | 0.0061 | | | −8.93 |
| Comp 2 (35) | 0.0058 | | | −3.57 |
| Comp 2 (88) | 0.0057 | | | −1.79 |
| Comp 2 (88) | 0.0060 | | | −14.29 |
| Comp 2 (175) | 0.0040 | | | 28.57 |
| Comp 2 (175) | 0.0055 | | | 1.79 |
| A (38)[1] | | 0.0136 | | 37.33 |
| A (38)[1] | | 0.0143 | | 34.10 |
| Blank | 0.0217 | | | |
| Comp 2 (88)[1] | 0.0206 | 0.0206 | | 5.07 |
| Comp 2 (88)[1] | 0.0200 | 0.0200 | | 7.83 |
| Blank | | | 0.0273 | |
| A (28)[2] | | | 0.0178 | 34.80 |
| A (28)[2] | | | 0.0185 | 32.23 |
| Comp 2 (88)[2] | | | 0.0263 | 3.66 |
| Comp 2 (88)[2] | | | 0.0264 | 3.30 |

[1] next 40% after top 10% removed
[2] combined top 10% and next 40% = top 50%
Comps 1 and 2 are commercially available nonylphenol-formaldehyde ethoxylates.
Treatment A is a 1:2 blend (actives) of a tallow triethoxyl quaternary amine acetate and a hydrogenated $C_{18}$ methyl chloride quaternary amine with 15 moles ethylene oxide.

Table VI demonstrates the superior results of the present invention at settling FCC slurry fines over conventional compounds. These results also evidence that the compounds of the present invention are effective over a varied range of actives dosages.

TABLE VII

Southern refinery
FCC slurry settling study
20 hours settling time at 160° F.
10% methods - solids

| Treatment (ppm) | Wt. in top 10 mL after 20 hours (g) | Avg. Wt. (g) | Weight of sample (g) | Wt. % | Avg. Wt. % |
|---|---|---|---|---|---|
| Comp 1 (75) | 0.012 | | 10.92 | 0.110 | |
| Comp 1 (75) | 0.008 | 0.010 | 10.52 | 0.076 | 0.093 |
| Comp 1 (150) | 0.009 | | 10.24 | 0.088 | |
| Comp 1 (150) | 0.013 | 0.011 | broken | — | 0.088 |
| Comp 1 (225) | 0.008 | | 11.01 | 0.073 | |
| Comp 1 (225) | 0.011 | 0.010 | 10.97 | 0.100 | 0.086 |
| A (37.5) | 0.009 | | 11.02 | 0.082 | |
| A (37.5) | 0.018 | 0.014 | 11.31 | 0.159 | 0.120 |
| A (75) | 0.010 | | 11.06 | 0.090 | |
| A (75) | 0.006 | 0.008 | 10.94 | 0.055 | 0.073 |
| A (112.5) | 0.019 | | 11.18 | 0.170 | |
| A (112.5) | 0.011 | 0.015 | 10.92 | 0.101 | 0.135 |

Comp 1 is a commercially available nonylphenol-formaldehyde ethoxylate.
Treatment A is a 1:2 blend (actives) of a tallow triethoxyl quaternary amine acetate and a hydrogenated $C_{18}$ methyl chloride quaternary amine with 15 moles ethylene oxide.

TABLE VIII

Northeast refinery
Slurry settling study
50% filterable solids method

| Treatment (ppm) | Solids in top 50% (g) | Solids in bot 50% (g) | % Settled | % Solids in top 50% | Ash in top 50% (g) | Wt. Ash in top 50% |
|---|---|---|---|---|---|---|
| Blank | 0.0124 | 0.2658 | 91 | 4.46 | 0.0026 | 0.005 |
| Blank | 0.0051 | 0.2483 | 96 | 2.00 | 0.0090 | 0.018 |
| A (37.5) | 0.0119 | 0.2295 | 90 | 4.93 | 0.0095 | 0.019 |
| B (43.2) | 0.0153 | 0.2598 | 89 | 5.89 | 0.0121 | 0.024 |
| C (14.2) | 0.0105 | 0.2510 | 92 | 2.95 | 0.0090 | 0.018 |
| C (20.0) | 0.0122 | 0.2328 | 90 | 4.98 | 0.0102 | 0.019 |
| D (79.8) | 0.0102 | 0.2560 | 92 | 3.8 | 0.0086 | 0.017 |
| E (79.8) | 0.0109 | 0.2307 | 91 | 4.51 | 0.0088 | 0.017 |
| F (79.8) | 0.0100 | 0.2433 | 92 | 3.94 | 0.0083 | 0.016 |

Treatment A is a 1:2 blend (actives) of a tallow triethoxy quaternary amine acetate and a hydrogenated $C_{18}$ methyl chloride quaternary amine with 15 moles ethylene oxide.
Treatment B is a commercially available quaternary ammonium compound available from Hoechst as DV-2423.
Treatment C is a tallow aminopropylamine pentamethyl chloride quat.
Treatment D is a $C_{18}$ aminopropylbisaminopropylamine nonamethyl stearate quat
Treatment E is a tallow diaminopropylamine heptamethyl chloride quat.
Treatment F is another tallow diaminopropylamine heptamethyl chloride quat.

These results demonstrate that the preferred embodiments of the present invention (Treatments A to F) provide effective settling aids of finely dissolved solids in hydrocarbons and FCC slurry fines in particular.

TABLE IX

Various refineries
Slurry settling study
75 ppm active treatment added

% Ash Settled

| Treatment | Southern Refinery Settled 14 days @ 170° F. 50% Method | Northeast Refinery Settled 6 days @ 170° F. 50% Method | Western Refinery Settled 14 days @ 70° F. 95% Method | | |
|---|---|---|---|---|---|
| A | 29 | 71.6 | — | 97.5 | 92.9 | 84.8 |
| B | 22 | 79.5 | — | 87.9 | — | — |
| C | 20 | 86.4 | 67.7 | 92.9 | — | — |
| Comp 1 | −17 | 65.0 | 70.2 | 97.8 | 93.1 | 84.8 |
| Blank | 21 | 71.7 | 58.3 | 91.8 | 87.8 | 75.3 |

Treatment A is a tallow triethoxyl quaternary amine acetate.
Treatment B is a hydrogenated $C_{18}$ methyl chloride quaternary amine with 15 moles ethylene oxide.
Treatment C is a 1:2 (actives) blend of Treatment A and Treatment B.
Comp 1 is a commercially available nonylphenol-formaldehyde ethoxylate.

As seen in Table IX, the compounds of the present invention both individually and in combination provide effective settling in fluids from different refineries.

TABLE X

Southern refinery
FCC slurry settling study
20 hours settling time at 160° F.
10% method: filterable solids

| Treatment (ppm active) | Wt. % Solids in top 10%* | % Reduction from blank |
|---|---|---|
| Blank | 0.0696 ± 7 | — |
| A (1 5.0) | 0.0757 ± 34 | −8.8 |
| A (37.5) | 0.0638 ± 4 | 8.3 |

TABLE X-continued

Southern refinery
FCC slurry settling study
20 hours settling time at 160° F.
10% method: filterable solids

| Treatment (ppm active) | Wt. % Solids in top 10%* | % Reduction from blank |
|---|---|---|
| A (75.0) | 0.0574 ± 24 | 17.5 |
| Comp 1 (17.0) | 0.0726 ± 4 | −4.3 |
| Comp 1 (42.5) | 0.0710 ± 22 | −2.0 |
| Comp 1 (85.0) | 0.0745 ± 3 | −7.0 |

*Average of duplicates ± range in last digits.
Treatment A is a 1:2 (actives) blend of a tallow triethoxylquaternary amine acetate and a hydrogenated $C_{18}$ methyl chloride quaternary amine with 15 moles ethylene oxide.
Comp 1 is a commercially available alkylphenol alkoxylate.

TABLE XI

Southern refinery
FCC slurry settling study
19 hours settling time at 150° F.
20% ash method

| Treatment (ppm active) | Wt. % Solids in top 20%* | % Reduction from blank |
|---|---|---|
| Blank | 0.0208 ± 3 | — |
| A (15.0) | 0.0222 ± 5 | −6.7 |
| A (37.5) | 0.0214 ± 0 | −2.9 |
| A (75.0) | 0.0206 ± 4 | 1.0 |
| Comp 1 (42.5) | 0.0212 ± 4 | −1.9 |
| Comp 1 (85.0) | 0.0228 ± 4 | −9.6 |

*Average of duplicates +/− range in last digit.
Treatment A is a 1:2 (actives) blend of a tallow triethoxylquaternary amine acetate and a hydrogenated $C_{18}$ methyl chloride quaternary amine with 15 moles ethylene oxide.
Comp 1 is a commercially available alkylphenol alkoxylate.

TABLE XII

Southern refinery
FCC slurry settling study
20 hours settling time at 150° F.
20% filterable solids and ash method

| Treatment (ppm active) | % Solids settled | % Ash settled* |
| --- | --- | --- |
| Blank | 62.6 | 67.2 |
| Blank | 48.9 | 66.3 |
| A (37.5) | 61.6 | 66.5 |
| A (75.0) | 53.5 | 55.5 |
| B (75.0) | 63.7 | 67.3 |
| B (150.0) | 59.3 | 63.5 |
| C (50.0) | 63.9 | 67.7 |
| C (100.0) | 61.5 | 66.2 |
| D (250.0) | 83.3 | 85.9 |
| D (500.0) | 95.7 | 101.9 |
| E (250.0) | 83.2 | 87.6 |
| E (500.0) | 93.4 | 98.5 |
| F (250.0) | 95.7 | 100.0 |
| F (500.0) | 91.4 | 96.2 |
| Comp 1 (42.5) | 53.4 | 60.5 |
| Comp 1 (85.0) | 45.8 | 47.6 |

*$(B - 4T)/(B + T)$

Treatment A is a 1:2 blend (actives) of a tallow triethoxyl quaternary amine acetate and a hydrogenated $C_{18}$ methyl chloride quaternary amine with 15 moles ethylene oxide.
Treatment B is a commercially available quaternary ammonium compound available from Hoechst as Dissolvan 2423.
Treatment C is a tallow aminopropylamine pentamethyl dichloride.
Treatment D is $C_{18}$ aminopropylbisaminopropylamine nonamethyl tetrastearate.
Treatment E is tallow diaminopropylamine heptamethyl tetrastearate.
Treatment F is tallow diaminopropylamine heptamethyl tetrastearate.
Comp 1 is a commercially available alkylphenol alkoxylate.

TABLE XIII

Southern refinery
FCC slurry settling study
20 hours settling time at 150° F.
20% filterable solids, top ash

| Treatment (ppm active) | % Solids settled* | Wt % Ash in top 20% |
| --- | --- | --- |
| Blank | 39.4 | 0.083 |
| A (63.4) | 59.2 | 0.076 |
| A (120.9) | 54.9 | 0.078 |
| B (62.8) | 63.1 | 0.071 |
| C (94.2) | 79.7 | 0.033 |
| C (115.0) | 80.3 | 0.017 |
| C (133.0) | 83.1 | 0.014 |
| Comp 1 (166.3) | 41.6 | 0.087 |

*$(B - 4T)/(B + T)$

Treatment A is a 1:2 blend (actives) of a tallow triethoxyl quaternary amine acetate and a hydrogenated $C_{18}$ methyl chloride quaternary amine with 15 moles ethylene oxide.
Treatment B is a tallow aminopropylamine pentamethyl dichloride.
Treatment C is tallow diaminopropylamino heptamethyl trichloride.
Comp 1 is a commercially available alkylphenol alkoxylate.

Tables XI–XIII demonstrate that the compounds of the present invention provide effective settling in hydrocarbon fluids. These results also demonstrate that the unethoxylated compounds provide equal to or better efficacy when compared to the ethoxylated compounds in this hydrocarbon fluid.

TABLE XIV

Southern refinery
Slurry settling summary
Treatment: 1:2 actives blend of a tallow triethoxyl quaternary amine acetate and a hydrogenated $C_{18}$ methyl chloride quaternary amine with 15 moles ethylene oxide, added as 15% active in hydrocarbon solvent to run down line to tankage.

| Feed Rate (ppm active) | Slurry Ash Content (%)* | |
| --- | --- | --- |
| | Untreated | Treated |
| 10.0 | 0.116 | 0.040 |
| 12.4 | 0.108 | 0.040 |
| 10.3 | 0.071 | 0.047 |
| 9.8 | 0.093 | 0.033 |
| 10.4 | 0.087 | 0.037 |

*Specification is ≦0.05%

These results show that the quaternary fatty ammonium compounds of the present invention are adequately effective at settling fines from untreated hydrocarbons.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

Having thus described the invention, what we claim:

1. A method for accelerating the settling of finely divided oil and water insoluble solids in hydrocarbon fluids comprising adding to said hydrocarbons an effective settling amount of a quaternary fatty ammonium compound having the formula

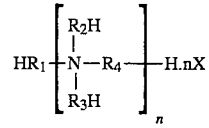

wherein $R_1$, $R_2$, $R_3$ and $R_4$ are $-R_5-$, $-(R_5O)_m-$, or

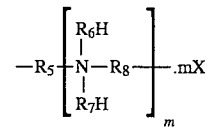

where $R_5$, $R_6$, $R_7$ and $R_8$ are $C_1$ to $C_{30}$ alkylene, alkenylene, or alkylarylidene, and m is 1–25, x is a halide, sulfate, nitrate, phosphate or carboxylate anion, and n is 1 to 50.

2. The method as claimed in claim 1 wherein said fatty ammonium compound is a methyl quaternary amine ethoxylate.

3. The method as claimed in claim 2 wherein said methyl quaternary amine ethoxylate is selected from the group consisting of tallow triethoxyl quaternary amine acetate and hydrogenated $C_{18}$ methyl chloride quaternary amine with 15 moles ethylene oxide.

4. The method as claimed in claim 1 wherein said quaternary fatty ammonium compound is a tallow amine alkyl quaternary compound.

5. The method as claimed in claim 4 wherein said tallow alkyl quaternary compound is selected from the group consisting of tallow aminopropylamine pentamethyl dichloride, tallow diaminopropyl heptamethyl trichloride and $C_{18}$ aminopropylbisaminopropylamine nonamethyl tetrastearate.

6. The method as claimed in claim 1 wherein said finely divided solids are fluid catalytic cracker catalyst fines.

7. The method as claimed in claim 1 wherein said hydrocarbon is a fluid catalytic cracker slurry.

8. The method as claimed in claim 1 wherein said hydrocarbon is selected from the group consisting of crude oils and fractions or residuals of crude oils boiling over about 400° F.

9. The method as claimed in claim 1 wherein said quaternary fatty ammonium compound is added to said hydrocarbon with at least one additional quaternary fatty ammonium compound.

10. The method as claimed in claim 1 wherein said quaternary fatty ammonium compound is added to said hydrocarbon in a range from about 1 part per million to about 500 parts per million parts hydrocarbon.

* * * * *